United States Patent
Ma et al.

(10) Patent No.: US 10,580,526 B2
(45) Date of Patent: Mar. 3, 2020

(54) SYSTEM AND METHOD FOR CALCULATING VESSEL FLOW PARAMETERS BASED ON ANGIOGRAPHY

(71) Applicant: Shenzhen Keya Medical Technology Corporation, Shenzhen (CN)

(72) Inventors: Bin Ma, Bellevue, WA (US); Xiaoxiao Liu, Bellevue, WA (US); Yujie Zhou, Beijing (CN); Youbing Yin, Kenmore, WA (US); Yuwei Li, Bellevue, WA (US); Shubao Liu, College Park, MD (US); Xiaoyang Xu, ShenZhen (CN); Qi Song, Seattle, WA (US)

(73) Assignee: Shenzhen Keya Medical Technology Corporation, Shenzhen (CN)

( * ) Notice: Subject to any disclaimer, the term of this patent is extended or adjusted under 35 U.S.C. 154(b) by 0 days.

(21) Appl. No.: 15/870,811

(22) Filed: Jan. 12, 2018

(65) Prior Publication Data
US 2019/0304592 A1    Oct. 3, 2019

(51) Int. Cl.
*G16H 30/40* (2018.01)
*G06T 7/246* (2017.01)
(Continued)

(52) U.S. Cl.
CPC ............ *G16H 30/40* (2018.01); *A61B 6/504* (2013.01); *G06T 7/251* (2017.01); *G06T 17/00* (2013.01);
(Continued)

(58) Field of Classification Search
CPC ........ G61H 30/40; G61H 50/50; G06T 7/251; A61B 6/504
See application file for complete search history.

(56) References Cited

U.S. PATENT DOCUMENTS

| 2014/0121513 A1* | 5/2014 | Tolkowsky ........ A61B 5/02007 600/431 |
| 2014/0200867 A1* | 7/2014 | Lavi ..................... G06F 19/321 703/2 |

(Continued)

OTHER PUBLICATIONS

Stalder, A.F. "Quantitative 2D and 3D Phase Contrast MRI: Optimized Analysis Blood Flow and Vessel Wall Parameters" Magnetic Resonance in Medicine (2008) (Year: 2008).*

(Continued)

*Primary Examiner* — Kim Y Vu
*Assistant Examiner* — Molly Delaney
(74) *Attorney, Agent, or Firm* — Bayes PLLC (57) ABSTRACT

The present disclosure relates to a device, a system, and a computer-readable medium for calculating vessel flow parameters based on angiography. In one implementation, the device includes a processor and a memory storing computer-executable instructions that, when executed by the processor, cause the processor to perform the following operations: selecting a plurality of template frames from the angiographic images to generate a 3D model for a vessel; determining a start frame and an end frame in the plurality of angiographic images showing a contrast filling process; determining corresponding locations of front ends of the contrast in the start frame and the end frame in the 3D model of the vessel; calculating a vessel volume between the determined locations of the front ends in the 3D model; and determining an average blood flow rate based on the calculated volume, and a time interval between the start frame and the end frame.

26 Claims, 3 Drawing Sheets

(51) Int. Cl.
*G16H 50/50* (2018.01)
*A61B 6/00* (2006.01)
*G06T 17/00* (2006.01)

(52) U.S. Cl.
CPC .............. *G16H 50/50* (2018.01); *A61B 6/481* (2013.01); *G06T 2207/10081* (2013.01); *G06T 2207/30104* (2013.01)

(56) References Cited

U.S. PATENT DOCUMENTS

| | | | | |
|---|---|---|---|---|
| 2015/0335304 | A1* | 11/2015 | Lavi | G06F 19/321 600/407 |
| 2015/0339847 | A1* | 11/2015 | Benishti | G16H 50/30 382/131 |
| 2015/0379230 | A1* | 12/2015 | Taylor | A61B 5/02007 703/11 |
| 2016/0110517 | A1* | 4/2016 | Taylor | A61B 5/02007 345/419 |
| 2017/0325770 | A1* | 11/2017 | Edic | A61B 6/5217 |
| 2018/0174490 | A1* | 6/2018 | Randles | G06T 7/0014 |
| 2018/0330507 | A1* | 11/2018 | Schormans | G06T 7/20 |
| 2018/0344173 | A1* | 12/2018 | Tu | A61B 5/02007 |

OTHER PUBLICATIONS

Nico H.J. Pijls et al., "Fractional Flow Reserve: A Useful Index to Evaluate the Influence of an Epicardial Coronary Stenosis on Myocardial Blood Flow," *Circulation*, vol. 92, No. 11 (1995), pp. 3183-3193.

Paul D. Morris, et al., "Virtual Fractional Flow Reserve From Coronary Angiography: Modeling the Significance of Coronary Lesions," *JACC: Cardiovascular Interventions*, vol. 6, No. 2 (2013), pp. 149-157.

Shengxian Tu, et al., "Fractional Flow Reserve Calculation From 3-Dimensional Quantitative Coronary Angiography and TIMI Frame Count," *JACC: Cardiovascular Interventions*, vol. 7, No. 7 (2014), pp. 768-777.

María J. Ledesma-Carbayo et al., "Spatio-Temporal Nonrigid Registration for Ultrasound Cardiac Motion Estimation," *IEEE Transactions on Medical Imaging*, vol. 24, No. 9 (Sep. 2005), pp. 1113-1126.

Gunnar Farnebäck, "Two-Frame Motion Estimation Based on Polynomial Expansion," *Scandinavian Conference on Image Analysis* (2003), pp. 363-370.

\* cited by examiner

SYSTEM AND METHOD FOR CALCULATING VESSEL FLOW PARAMETERS BASED ON ANGIOGRAPHY

TECHNICAL FIELD

The present disclosure relates to a method, a system, and a computer-readable medium for calculation and analysis based on human physiology and hemodynamics, and, more particularly, to a method, a system, and a computer-readable medium for calculating vessel flow parameters based on angiography.

BACKGROUND

One main cause of coronary heart disease is coronary stenosis caused by arteriosclerosis. Coronary stenosis can cause significant changes in coronary blood flow and other hemodynamics, as well as lead to relative and absolute myocardial ischemia. Coronary angiography and intravascular ultrasound are the most common techniques for diagnosing coronary heart disease. X-ray angiography (hereinafter referred to as X-ray radiography) is an X-ray imaging system which combines conventional angiography and electronic computer image processing technology. By injecting a contrast agent into a blood vessel, X-ray radiography can dynamically observe, from different orientations (i.e., from different projection view angles), the shape and state of the vessel and any lesions thereof, as well as flow dynamics. X-ray radiography is generally adapted for examining large vessels of the heart, such as a coronary artery, as well as cervical and intracranial arteries, and is often used for diagnosing and observing arterial stenosis, occlusion, blood vessel development abnormality and blood supply conditions.

For interventional technologies, especially blood vessel reconstruction, X-ray radiography is generally required. However, the degree of stenosis evaluated through such images is not directly associated with blood flow supply and ischemic condition at the distal end of a blood vessel tree. Since 1995, a new index, the Fractional Flow Reserve (FFR), has been proposed for calculating coronary blood flow through a pressure measurement. FFR has become important for functionally evaluating coronary stenosis, and an important guiding tool for coronary revascularization. However, FFR measurement based on a pressure guide wire usually serves as an invasive intrusion measurement and may even cause a risk of trauma.

With advances in medical imaging technology and reconstruction technology, computational fluid mechanics, high-performance computing and other fields, numerical simulation calculation of FFR (virtual FFR) is a recent development. According to clinical tests, virtual FFR, which may be specific to the scale of each blood vessel level of the patient individual, generally has a very high capability to diagnose myocardial ischemia with high accuracy, sensitivity, specificity, positive and negative prediction values, compared with conventional methods.

At present, calculation methods for virtual FFR mainly include $FFR_{CT}$ based on coronary angiography CT, FFR simulation vFFR based on X-ray radiography image and $FFR_{QCA}$ based on the combination of quantitative coronary angiography with a TIMI (Thrombolysis In Myocardial Infarction) frame count method. Calculation precision and computation time are standards for judging which calculations methods are best for clinical popularization.

SUMMARY

Extant calculation methods of the virtual FFR have various problems.

In terms of treatment time, it may take as long as 145 hours to calculate using $FFR_{CT}$. vFFR based on X-ray radiography technology uses general boundary conditions for calculation, but the general boundary conditions cannot characterize a physiological condition specific to an individual patient, and accordingly reduces the accuracy of the calculation result.

$FFR_{QCA}$ may obtain a more accurate flow rate/flow boundary conditions using image processing, thereby avoiding the complexity and uncertainty on account of the whole blood vessel tree network model and microvascular resistance estimation. The method may directly apply the boundary conditions specific to the patient to the lesion vessel, and the optimal time may be shortened to be within 10 minutes. However, $FFR_{QCA}$ requires the TIMI frame count method.

In terms of accuracy, a major challenge that virtual FFR (which is usually a computational fluid dynamics (CFD) simulation) calculation presents is how to obtain/set the physiological boundary condition specific to the patient both conveniently and quickly. Whether the boundary conditions reflect the individual will determine, to a large extent, the accuracy of the calculation and whether the boundary conditions can be obtained conveniently and quickly will influence the duration of the calculation and its clinical applicability. Although the TIMI frame count method can be used for estimating the flow rate and providing better boundary conditions specific to the patient, extant processing methods require a skilled analyst. Particularly, the skilled analyst is required to select, from the sequence of the angiographic image frames of the vessel, a sub-sequence of frames clearly reflecting the contrast filling process, to mark out a landmark of an anatomical structure on the image frames, to obtain the contrast transfer time by calculating the number of frames experienced until the contrast fills to the landmark, after which an average blood flow rate is obtained by dividing the length or volume of the vessel segment filled with the contrast during the contrast transfer period by the contrast transfer time, which then serves as the boundary condition of the CFD model. This results in at least the following technical problems: the accuracy and the duration are dependent on the professional level of the analyst, which is prone to manual error and increases in processing time; an average volume flow while filling is calculated by dividing the inner cavity volume of the reconstructed vessel tree by the average transfer time of the contrast, and the start frame and the end frame of the contrast transfer period cannot be automatically selected; and during the contrast filling period, the vessel often moves (for example, a coronary artery may physically move due to a cardiac cycle), which causes inaccurate calculation of the length or volume of the vessel segment through which the contrast passes during the filling period.

When diagnosing the vessel lesion, a doctor may also use blood flow parameters other than FFR for reference, such as blood flow, blood flow rate, blood pressure, micro vascular resistance, etc.

Therefore, there is a need for a method and a device capable of rapidly and accurately establishing the physiological boundary condition with respect to the patent individual for the CFD simulation of the vessel flow parameters based on angiography. Computer languages (such as Python and Bash Script) may be used for writing the processing steps as instructions into a computer readable storage medium to automatically realize the whole calculation process of the physiological boundary condition when executed by a computer, such as a processor. There is also a need for a system for CFD simulation of vessel flow parameters based on angiography. By using the above method and/or above device to establish the physiological boundary condition specific to the patient, computer languages (such as Python and Bash Script) may be used to implement the disclosed method.

Embodiments of the present disclosure provide a method and a device for rapidly and accurately establishing the physiological boundary condition specific to the patient for CFD simulation of vessel flow parameters based on angiography. According to a first aspect of present disclosure, a device for modeling a vessel based on angiographic images, the device may comprise an interface configured to receive the angiographic images acquired by an angiography imaging device; a processor; and a memory storing computer-executable instructions that, when executed by the processor, cause the processor to perform one or more operations. The operations may comprise selecting a plurality of template frames from the angiographic images to generate a 3D model for a vessel; determining a start frame and an end frame in the plurality of angiographic images showing a contrast filling process; determining corresponding locations of front ends of the contrast in the start frame and the end frame in the 3D model of the vessel; calculating a vessel volume between the determined locations of the front ends in the 3D model; and determining an average blood flow rate based on the calculated volume, and a time interval between the start frame and the end frame.

A physiological boundary condition for a simulation of the vessel may be blood flow (that is, blood flow volume rate) and may alternatively or additionally be various vessel flow parameters obtained by processing on the blood flow, such as flow rate, micro vesicular resistance, etc. The present disclosure provides a vessel matching and tracking algorithm with respect to the blood flow realized by a computer and based on angiographic image frames. The disclosed algorithm may be widely applied to radiography-based imaging data of myocardium, carotid artery, and lung blood vessels, etc., to obtain blood flow information. The method and system disclosed herein may automatically analyze radiography-based image frames and automatically extract vessel flow parameters to use as the physiological boundary condition, thereby significantly reducing manual error, workload and processing time for an operator, and improving the accuracy and flexibility of the calculation of vessel flow parameters of the patient.

In some embodiments, the operations may further comprise using the obtained average blood flow rate as boundary conditions for computational fluid dynamics simulation of the vessel.

In some embodiments, selecting a plurality of template frames may comprise selecting image frames filled with the contrast from an image frame sequence of two view angles satisfying reconstruction conditions.

In some embodiments, the reconstruction conditions may include that an angle between the two view angles is greater than or equal to a predetermined angle and may further include the following condition: a vessel segment of interest is fully filled with contrast agent and vessel boundaries are visible.

In some embodiments, determining the start frame and the end frame may be based on at least one of:

a contrast sharpness in the angiographic images;
a maximum time interval of the contrast flowing through a single branch of the vessel; and a temporal change of pixel values near markers in the angiographic images.

In some embodiments, the start frame and the end frame may correspond to the same view angle.

In some embodiments, the same view angle may be one of two view angles used to select the template frames.

In some embodiments, determining the corresponding locations of the front ends of the contrast in the start frame and the end frame may be based on patch matching of the frames.

In some embodiments, determining the corresponding locations may include:

extracting multiple patches along a central line of the vessel in the template frames;

finding corresponding locations with a maximum correlation coefficient within a corresponding neighborhood in the start frame and the end frame based on the respective patches in the template frames to determine corresponding patches in the start frame and the end frame; and determining a patch not presenting the vessel in the corresponding patches in the start frame and the end frame and determining the corresponding locations of the front ends of the contrast in the start frame and the end frame based on the determined patch.

In some embodiments, determining the corresponding locations of the front ends of the contrast in the start frame and the end frame may be based on vessel matching between the start frame and the template frames and between the end frame and the template frames, and the vessel matching may include non-rigid matching or optical flow calculation.

The present disclosure further provides a computer-implemented method for calculating a vessel flow parameter based on angiography.

The method may comprise:

selecting a plurality of template frames from a plurality of angiographic images to generate a 3D model for a vessel;

determining a start frame and an end frame in the plurality of angiographic images showing a contrast filling process;

determining corresponding locations of front ends of the contrast in the start frame and the end frame in the 3D model of the vessel; calculating a vessel volume between the determined locations of the front ends in the 3D model;

determining an average blood flow rate based on the calculated volume, and a time interval between the start frame and the end frame; establishing a 3D computational fluid dynamics model for a segment of the vessel and setting boundary conditions thereof based the obtained average blood flow rate; and solving the established 3D computational fluid dynamics model to obtain the vessel flow parameter at an individual position of the vessel segment.

Systems and methods of the present disclosure may quickly and accurately obtain a functional evaluation of a lesion vessel specific to the patient, including evaluation of the impact of a suspected lesion position, the culprit lesion, and the lesion on myocardial ischemia, and complex vascular stenosis conditions (such as single-branch and multi-branch vascular lesions, multi-position lesions of the same vessel, moderate stenosis lesions, continuous lesions, diffuse lesions, restenosis in a stent, and the like). On account of the rapid and accurate calculation of vessel flow parameters as physiological boundary conditions, methods and systems of the present disclosure that perform a CFD simulation of vessel flow parameters based on angiography improve the simulation in terms of accuracy and efficiency. Some embodiments of the present disclosure may complete the calculation and processing of a single case within 5-10 minutes, enabling large-batch processing as well as real-time processing of cases, compared with extant techniques for which the time for calculating each case may be hours.

In some embodiments, the method may further comprise using the obtained average blood flow rate as boundary conditions for the 3D computational fluid dynamics model.

In some embodiments, selecting a plurality of template frames may comprise selecting image frames filled with the contrast from an image frame sequence of two view angles satisfying reconstruction conditions.

In some embodiments, the reconstruction conditions may include that an angle between the two view angles is greater than or equal to a predetermined angle and may further include the following condition: a vessel segment of interest is fully filled with contrast agent and vessel boundaries are visible.

In some embodiments, determining the start frame and the end frame may be based on at least one of:
a contrast sharpness in the angiographic images;
a maximum time interval of the contrast flowing through a single branch of the vessel; and a temporal change of pixel values near markers in the angiographic images.

In some embodiments, the start frame and the end frame may correspond to the same view angle.

In some embodiments, the same view angle may be one of two view angles used to select the template frames.

In some embodiments, determining the corresponding locations of the front ends of the contrast in the start frame and the end frame may be based on patch matching of the frames.

In some embodiments, determining the corresponding locations may include:
extracting multiple patches along a central line of the vessel in the template frames;
finding corresponding locations with a maximum correlation coefficient within a corresponding neighborhood in the start frame and the end frame based on the respective patches in the template frames to determine corresponding patches in the start frame and the end frame; and determining a patch not presenting the vessel in the corresponding patches in the start frame and the end frame and determining the corresponding locations of the front ends of the contrast in the start frame and the end frame in the template frames based on the determined patch.

In some embodiments, determining the corresponding locations of the front ends of the contrast in the start frame and the end frame may be based on vessel matching between the start frame and the template frames and between the end frame and the template frames, and the vessel matching may use non-rigid matching or optical flow calculation.

In some embodiments, the method may further comprise writing the vessel flow parameter at the individual position of the segment into a case analysis report for reference by doctors.

In some embodiments, the angiographic images may be collected under a resting condition, and setting the boundary conditions may include: multiplying the obtained average blood flow rate by 3-3.5 times to convert the average blood flow rate into an average blood flow rate under a hyperemia condition, and setting the boundary conditions based on the average blood flood rate under a hyperemia condition.

In some embodiments, the average blood flow rate between the start frame and the end frame may characterize the average blood flow in the segment.

In some embodiments, determining the corresponding locations of the front ends of the contrast in the start frame and the end frame may be based on the contrast filling process in the segment, such that the average blood flow rate between the start frame and the end frame may characterize the average blood flow rate in the segment.

In some embodiments, determining the start frame and the end frame may include at least one of:
determining the start frame and the end frame such that the contrast filling process between the start frame and the end frame passes through the entire segment without any branch; and setting an inlet marker near a start point and an outlet marker near an end point of the segment in the angiographic images, and automatically selecting the start frame and the end frame by analyzing variations of pixel values near the inlet marker and the outlet marker over time.

The present disclosure further provides a non-transitory computer-readable storage medium storing computer executable instructions, wherein the computer-executable instructions, when executed by a processor, cause the processor to perform the following operations:
selecting a plurality of template frames from a plurality of angiographic images to generate a 3D model for a vessel;
determining a start frame and an end frame in the plurality of angiographic images showing a contrast filling process;
determining corresponding locations of front ends of the contrast in the start frame and the end frame in the 3D model of the vessel;
calculating a vessel volume between the determined locations of the front ends in the 3D model; and
determining an average blood flow rate based on the calculated volume, and a time interval between the start frame and the end frame.

BRIEF DESCRIPTION OF THE DRAWINGS

Embodiments of the present disclosure are described in detail with reference to the accompanying drawings, which are not to be construed as limiting. The features, advantages, and techniques and applicability of the exemplary embodiments of the present disclosure are described below with reference to the accompanying drawings in which like reference numerals refer to like elements.

DETAILED DESCRIPTION

Figure 1:
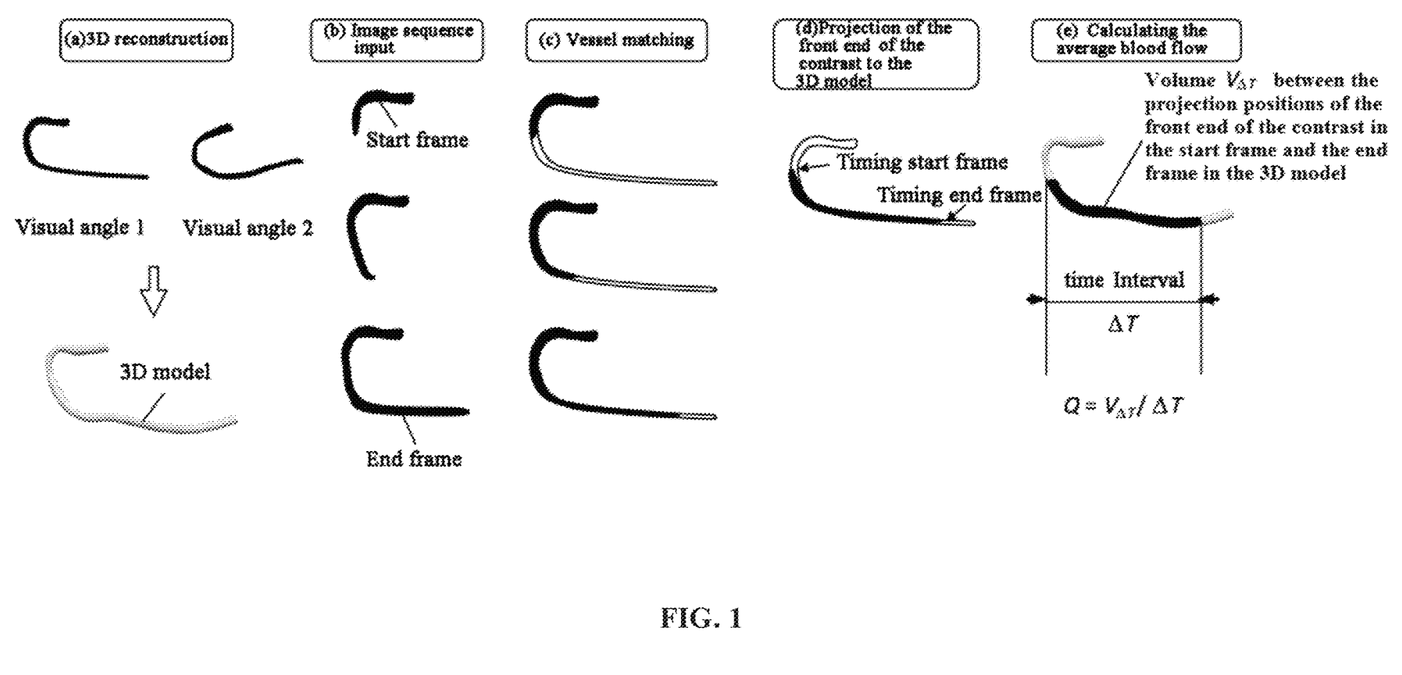
FIG. 1 shows a flow schematic diagram of an exemplary calculation of blood flow in a vessel as the boundary condition of a CFD simulation of the vessel, according to an exemplary embodiment of the disclosure.

The present disclosure provides a method for calculating a vessel flow parameter based on an angiographic image frames sequence. Although the calculated vessel flow parameter may not be accurate enough to be directly used for medical diagnosis, the parameter may be used as the boundary condition of a CFD simulation of the vessel flow parameter using FFR for diagnosis. An example of the method is shown in FIG. 1 and comprises: selecting a plurality of template frames from a plurality of angiographic 2D image frames to generate a 3D model for the vessel (depicted as step (a) in FIG. 1). Various techniques may be used to perform this step, e.g., vessel segmentation and generation of a central line, then reconstruction of a surface model of the vessel central line and the vessel in a 3D space. The method further comprises determining a start frame and an end frame of a contrast filling process (depicted as step (b) in FIG. 1); determining corresponding locations of the front ends of the contrast in the start frame and the end frame in the template frame (depicted as step (b) in FIG. 1) to project the front ends into the 3D model of the vessel (depicted as step (d) in FIG. 1); and calculating a volume between the projected locations of the front ends and dividing the calculated volume by the time between the start frame and the end frame to obtain an average blood flow rate (depicted as step (e) in FIG. 1).

As used herein, the term "template frame" refers to specific 2D image frames used for 3D reconstruction. 2D image frames of two (visual) angles may be used for the 3D reconstruction, and generally satisfy the reconstruction conditions, for example, that an angle between the two angles is no less than 30 degrees, that the vessel of interest is clearly visible and is filled with the contrast in the 2D image frames, etc. As used herein, the term "flowing frame" refers to a set of frames that are relatively clear and visible in the contrast flowing process, and may include all the frames of the whole flowing process from when the contrast is filled into the interested vessel until the interested vessel is fully filled with the contrast. The vessel flow parameters used as the physiological boundary condition of the vessel CFD simulation may be different from the vessel flow parameters at an individual position of the vessel obtained from the vessel CFD simulation. The former may include blood flow, and may also include various vessel flow parameters obtained based upon the blood flow, such as flow rate, micro vesicular resistance, etc. These parameters usually cannot be used for diagnosis directly, but may serve as intermediate information, e.g., as the physiological boundary condition. The latter include the parameters at the individual position of the vessel obtained by the vessel CFD simulation, including FFR, blood flow, blood flow rate, blood pressure, micro vascular resistance, etc.

A detailed description of the steps of the method is provided below.

Step 1: selecting a plurality of template frames from a plurality of angiographic 2D image frames. The plurality of template frames may be used for vessel segmentation and for generating a central line, then for reconstructing a surface model of the vessel central line and the vessel in a 3D space. In one embodiment, during the 3D reconstruction process, the image frames substantially filled with the contrast may be selected as the template frames based on two view angles satisfying the reconstruction conditions (for example, that the two view angles form an angle of no less than 30 degrees with each other, that the vessel of interest is clearly visible, etc.) and used for vessel segmentation and for generating the central line. In one embodiment, the template frames may be automatically selected by the computer based on the reconstruction conditions, for example, by selecting 2D image frames at an angle of more than 30 degrees with each other, in which the vessel of interest is substantially filled with the contrast and is clearly visible. In certain aspects, the contrast filling time may be set in advance according to experience and/or historical data associated with the patient, and the vessel may be assumed to be substantially filled with the contrast after such time elapses.

Accordingly, the 2D image frames after the contrast filling time elapses may be automatically assumed to be the image frames filled with the contrast. In one embodiment, the definition (i.e., clarity) of the blood vessel may be calculated, and a 2D image frame having clarity above a clarity threshold may be assumed to have clear vessels. A plurality of extanth image clarity evaluation functions, including but not limited to the Brenner gradient function, the Tenengrad gradient function, the sum-modulus-different (SMD) (or gray variance) function, the energy gradient function, the edge sharpness-based edge acutance value (EAV) point sharpness algorithm function, a quadratic fuzzy-based clarity algorithm and the like, may be used for calculating the clarity of the vessel. Using the template frames, the surface model of the vessel central line and the vessel may be reconstructed in the 3D space using polar plane constraint and projection error optimization. Other techniques for 3D reconstruction using the template frames may include, for example, a plurality of open source software modules, including vmtk (the Vascular Modeling Toolkit), which may be used for calculating and reconstructing the vessel central line and a vessel wall of the vessel tree based on the results of vessel analysis and segmentation on the template frames to construct a 3D geometric model of the vessel. For the 3D reconstruction process, a 3D structure of the vessel may be generated by combining the images and the central lines in the template frames; therefore, each point on the vessel 2D central line at the two angles may have a corresponding (i.e., one-to-one) point on the reconstructed 3D central line.

Step 2: determining a start frame and an end frame of the contrast filling process. X-ray angiogram technology may be used for visualizing the flow of blood in the vessel, and may be further used for quantitatively estimating blood flow parameters, such as volume flow and flow rate. The average volume flow Q of blood is defined as the volume of blood flowing within unit time, $Q=V_{\Delta T}/\Delta T$, where $\Delta T$ is the time interval between the start frame, in which the contrast flows through an inlet marker of the vessel, and the end frame, in which the contrast flows through an outlet marker of the vessel, and $V_{\Delta T}$ is a volume of blood flowing between the two frames (that is, the volume of the contrast filling and extending). The precision of this average flow estimation depends upon selection of appropriate start and end frames.

The blood flow of a patient may be estimated accurately by ensuring a sufficient sampling period. In an example with a coronary angiography image, the blood flow therein is generally affected by the cardiac cycle of the patient, and if the start frame and the end frame in a part of the cardiac cycle are used, the blood flow of the patient will not be calculated accurately, but selecting the start frame and the end frame such that they span a plurality of cardiac cycles usually results in more accurate average flow information.

In order to improve the accuracy of average flow estimation, the two flowing frames (i.e. the start frame and the end frame) used for calculating the blood flow may be automatically selected based on contrast clarity, and the above mentioned clarity algorithms may be applied to the calculation of the contrast clarity. For example, in the image frame sequence of the contrast filling process, the frames near the start and the end in which the contrast clarity exceeds the threshold may be automatically selected as the start frame and the end frame, respectively. In one embodiment, the start frame and the end frame may be automatically selected based on the maximum interval on a single vessel. Because the blood flow may diverge at a branch of the vessel tree, by using the maximum interval on the single vessel, it may not only ensure a sufficient sampling period, but also facilitate the calculation of the volume through which the blood flows. For example, the maximum interval on the single vessel may be set in advance according to experience and/or historical data. In addition, when the contrast flows through a certain point, the gray value of the point is typically reduced, the automatic selection method may analyze variations of image gray values near the markers. In certain aspects, the inlet marker and the outlet marker may be set in advance on the image frame. When the image gray value near the inlet marker is detected as reduced, the image frame at such time point may be taken as the start frame, and when the image gray value near the outlet marker is detected as reduced, the image frame at such time point may be taken as the end frame.

In order to quantitatively calculate the volume through which the blood flows, the front end of the contrast on each 2D image (in the flowing frames), which generally characterizes the blood flowing conditions at each time point, may be projected onto the 3D model of the vessel. Accordingly, in some embodiments, the corresponding locations of the front ends of the contrast in the start frame and the end frame in the template frames may be determined.

Step 3: determining corresponding locations of the front ends of the contrast in the start frame and the end frame in the template frames. In some embodiments, only the image frame of one angle is used for the subsequent image-based extraction of blood flow parameters, and a set of frames within which the flowing process is relatively clear and visible may be selected as the flowing frame. The image itself in the template frame and the 2D vessel central line extracted therefrom may be used as the input for analyzing the flowing condition of the contrast in the flowing frame. For example, from an image frame sequence, the image with one angle showing a relatively clear and visible flowing process may be selected as the flowing frame. Accordingly, the corresponding position of the front end of the contrast in the flowing frame as in the template frame at the same angle may be calculated. Because position matching is generally easier between the image frames with the same angle, distortion and deformation caused by the angle difference may also be reduced and matching efficiency improved.

Figure 2:
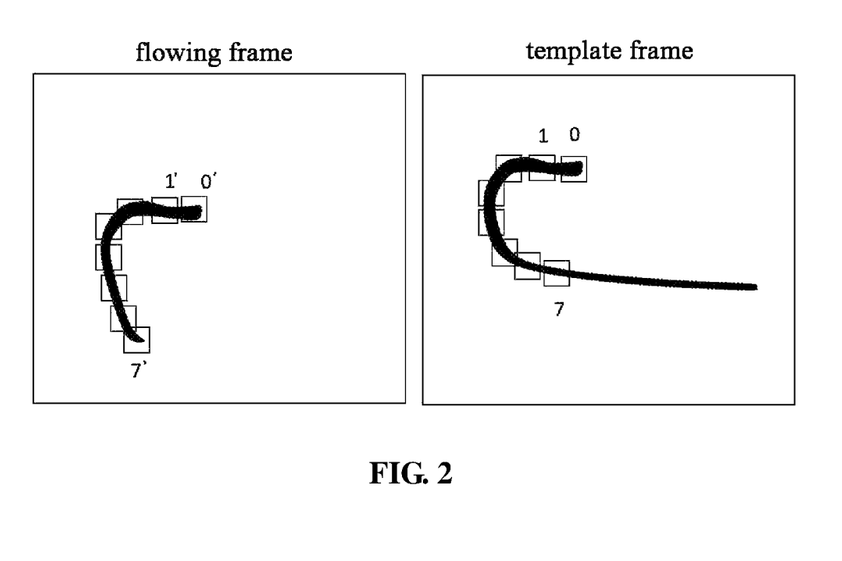
FIG. 2 shows a schematic diagram of an example of matching and tracking a vessel in angiographic image frames, according to an exemplary embodiment of the disclosure, where the left side is the flowing frame and the right side is the template frame.

Many techniques may be used for determining the corresponding locations of the front ends of the contrast in the start frame and the end frame in the template frames. For example, an algorithm based on module matching between vessel images may be used. FIG. 2 shows a schematic diagram of an example of matching and tracking the vessel in angiographic image frames. The left side is the flowing frame, and the right side is the template frame to be matched. Taking the 2D vessel central line and the corresponding vessel image thereon in the template frame as inputs, with the point coordinates on the vessel central line of the template frame as centers, patches with the size of, for example, 30 pixels*30 pixels may be extracted along the filling direction (patches 0-7 are depicted in the right side of FIG. 2). First, based on patch 0 in the template frame, the corresponding position of the maximum correlation coefficient may be found through convolution in the corresponding neighborhood within the flowing frame to determine the start position and the start image patch (that is, patch 0') of the vessel in the flowing frame. For example, the position of patch 0 in the template frame may be used as the center for setting a neighborhood near the center in the flowing frame, after which convolution may be performed between each of the patches (e.g., of size 30 pixels*30 pixels). Accordingly, patch 0' corresponding to the maximum correlation coefficient may be found as the patch which represents the vessel start position in the flowing frame. Next, and similarly, based on the patch n (where n is an integer) in the template frame, the corresponding location of the maximum correlation coefficient within the corresponding neighborhood in the flowing frame may be determined through convolution, resulting in the corresponding patch n' in the flowing frame. For example, the following method may be used: using the position of patch n in the template frame as the center, setting a neighborhood near the center, performing convolution between each of the patches of 30 pixels*30 pixels with the point in the neighborhood as the center and the patch n in the template frame, and finding the patch n' corresponding to the maximum correlation coefficient as the corresponding patch in the flowing frame.

In one embodiment, the vector formed between adjacent points of the vessel central line may be used to combine the correlation coefficient of each patch in the template frame and the corresponding individual patch in the flowing frame to complete the matching and the tracking of the vessels in the flowing frame and in the template frame. As shown on the right side of FIG. 2, in one example, for the vessel patches in the template frame, sequentially (e.g., starting with 0, patch 0 representing the start patch) finding the most relevant vessel position in the flowing frame and visualizing the position may be performed using a square window (e.g., the $n^{th}$ image patch found in the flowing frame corresponding to the $n^{th}$ image patch in the template frame). When the vessel is no longer included in the window found in the flowing frame, vessel tracking may end (as depicted in the example of FIG. 2, patch 7 is the last image patch containing the vessel). At the same time, for the front end (e.g., corresponding to the most downstream position at which the contrast flows) of the contrast in the flowing frame, the corresponding position thereof in the template frame may also be determined. For example, the position of the front end of the contrast in the flowing frame may correspond to the position within patch 7 in the template frame. This algorithm may account for global movement and local deformation of the vessel in the flowing frames, and also achieve automatic, accurate, and rapid vessel tracking.

In some embodiments, this step may also be realized by determining the position of the front end of the contrast in the flowing frame in combination with the vessel matching between the flowing frame and the template frame. The vessel matching may be implemented using various techniques.

In some embodiments, vessel matching may also be implemented by non-rigid matching based on image gray values. This method attempts to find the match of each pixel on the image (or in an area of interest on the image) among different frames in a sequence. This method calculates the local motion vector of each pixel by calculating the displacement between matched pixels on different frames. This method needs to solve a more complex global optimization problem in order to find the optimal matching and usually requires relatively accurate initial parameter estimation.

In some embodiments, vessel matching may also be implemented by calculating the optical flow between two frames. Optical flow refers to the instantaneous speed of pixel motion of a spatial moving object on an observation imaging plane and is generally caused by movement of a foreground object itself, movement of a camera, or both. An optical flow field is a 2D instantaneous speed field formed by pixels in an image. Optical flow estimation is a method for finding the position correspondence between two frames using temporal variations of pixels in the two image frames to calculate motion information of the vessel between two frames.

When vessel matching is complete, the position of the front end of the contrast in the flowing frame may be determined using extant image processing algorithms or deep learning-based image segmentation, optionally in combination with any one of: accounting for the continuity of the contrast flowing in the time dimension, accounting for global information, and/or using algorithms such as Graph-cut, conditional random field (CRF) or a recursive neural network (RNN). By determining the position of the front end of the contrast in the flowing frame in combination with vessel matching between the flowing frame and the template frame, the corresponding position in the template frame of the front end of the contrast in the flowing frame (e.g., the start frame or the end frame) may be determined.

Step 4: projecting the front ends into the 3D model of the vessel. After determining the corresponding positions of the front ends of the contrast in the template frame, the 2D position may be further projected into the 3D reconstructed vessel surface model (as shown in step (d) of FIG. 1) using a reconstruction relation. The volume between the start frame and the end frame within the 3D model may be obtained using divergence theorem and/or using integration based on the radius and length of the vessel central line. The obtained volume may be divided by the corresponding time to obtain volume flow per unit time (as shown in step (e) of FIG. 1). The volume flow may be used as the flow boundary condition for CFD calculation of various vessel parameters, including FFR.

Although the method for calculating blood flow based on an angiographic image frame sequence is illustrated and exemplified in the above example in which blood flow is calculated, other vessel flow parameters may be obtained using alternative or additional processing. For example, the blood flow rate may be obtained by dividing the calculated blood flow by the sectional area of the vessel; micro vessel resistance may be obtained by dividing pressure at the outlet of the vessel by the calculated blood flow; and the like.

The steps of the above example method for automatically calculating vessel flow parameters based on an angiographic image frame sequence may be stored as instructions in a computer-readable storage medium, such that the method is performed when the instructions are executed by a processor. The computer-readable storage medium and the instructions stored thereon, optionally with the processor, may form a device for calculating vessel flow parameters based on angiography.

Figure 3:
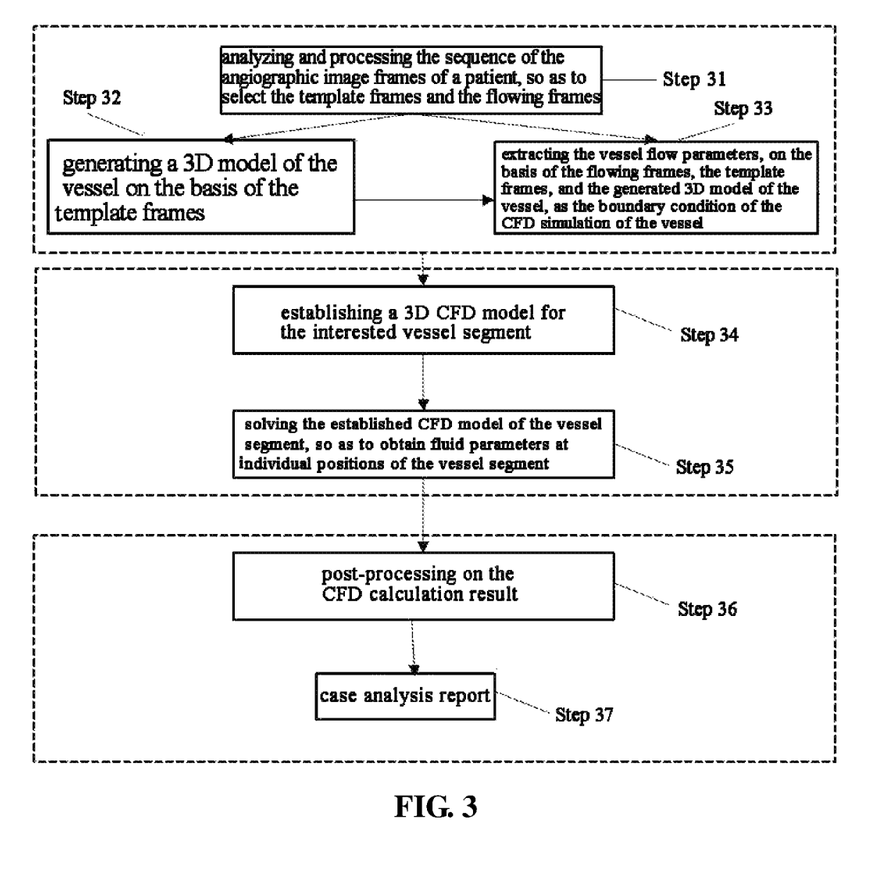
FIG. 3 shows an overall flow diagram of an exemplary 3D CFD simulation of a vessel, according to an exemplary embodiment of the disclosure.

FIG. 3 shows an overall flow diagram of an example 3D CFD simulation of the vessel according to another embodiment of the present disclosure.

As shown in FIG. 3, the overall method may include: analyzing and processing the sequence of angiographic image frames of a patient to select a plurality of template frames and flowing frames (e.g., a start frame and an end frame) (depicted as step 31); generating a 3D model of the vessel based on the template frames, for example, by performing vessel segmentation and generating a central line for the template frame, then reconstructing a surface model of the vessel central line and the vessel in a 3D space (depicted as step 32); extracting one or more vessel flow parameters based on the flowing frames, the template frames, and the reconstructed 3D model of the vessel, and using the one or more vessel flow parameters as the boundary condition of a CFD simulation of the vessel (depicted as step 33). Steps 31-33 are described above in detail. In steps 31-33, a segment of interest of the vessel may be selected for the 3D reconstruction rather than the entire vessel. For example, based on vessel segment of interest, the start frame and the end frame of the contrast filling process may be determined, such that the average blood flow between the start frame and the end frame characterizes the average blood flow in the vessel segment of interest. For example, during the contrast filling process between the start frame and the end frame, the contrast may pass through the entire vessel segment of interest without passing through any branch. In this example, an inlet marker and an outlet marker may be set in advance respectively near the start point and the stop point of the vessel segment of interest in one or more frames. By monitoring the reduction of image gray values near the inlet and outlet markers, the start frame and the end frame may be determined, respectively. This only serves as an example, and determining the start frame and the end frame of the contrast filling process based on a vessel segment of interest is not limited thereto.

Moreover, the overall method may further include:

establishing a 3D CFD model for the vessel segment of interest (depicted as step 34). After the extracted vessel flow parameters are applied as the boundary condition to the inlet and the outlet of the corresponding vessel, meshes may be generated for the 3D model of the vessel segment of interest. For example, the inlet flow and the outlet flow of the vessel segment may be set to the average blood flow in the vessel segment. One or more physical properties and/or a flow equation of blood may also be set. Various open source software modules, such as vmtk, tetgen, etc., may be used for generating high-quality meshes satisfying the CFD calculation requirements for the 3D model of the vessel. The 3D reconstruction may be performed only for the vessel segment of interest, and meshes may be generated only for the reconstructed 3D model of the vessel segment of interest. Alternatively, the 3D reconstruction may be performed for a vessel segment including the vessel segment of interest, and the vessel segment of interest in the reconstructed 3D model may be selected to generate meshes. The former technique saves calculation resources while the latter technique enables a user to view the 3D model of the vessel segment to select the vessel segment of interest therefrom with the selection being more visual and convenient.

The established CFD model of the vessel segment may be solved based on the inlet boundary condition and the outlet boundary condition, the set of physical properties and the flow equation of blood to obtain fluid parameters at an individual position of the vessel segment (depicted as step 35). Alternatively or concurrently, post-processing may be performed on the obtained fluid parameters to obtain vessel flow parameters, such as FFR, at the individual position of the vessel segment for use in diagnosis (depicted as step 36). In some embodiments, the vessel flow parameters used for diagnosis may be written into a case analysis report for reference by doctors (depicted as step 37).

In one embodiment, in step 34, the boundary conditions may be set as follows:

The inlet boundary condition may be set by applying an inlet flow specific to a patient and an average aortic pressure (e.g., based on a large amount of clinical measurements) to an outlet boundary.

The outlet boundary condition may be set by applying an outlet flow specific to a patient, assuming that at the outlet fluid is completely developed and the pressure gradient is zero.

Both the inlet flow and the out flow specific to a patient may be set to the average flow under the hyperemia condition in the vessel segment. The calculated volume flow (for example, by using the calculation method described above in combination with FIG. 1) may serve as the average blood flow in the vessel segment. In some embodiments, angiography may be completed while the patient is resting, and the blood flow may be calculated as explained above based angiography performed during resting, and may be converted, by multiplying by 3-3.5 times, to obtain the blood flow under the hyperemia condition. According to the definition of FFR, FFR is the fractional flow reserve under the hyperemia condition, and generally requires the blood flow under the hyperemia condition as the boundary condition for use in the simulation calculation. With the technique described above for obtaining the boundary condition of the CFD simulation under the hyperemia condition based on angiography performed during resting, a patient does not need to take medicines to achieve hyperemia. Rather, because the clinical user effect is equivalent to determining the blood flow on the basis of various measurements under the hyperemia condition as the boundary condition, the above technique reduces medicine intake and relieves pain of the patient.

In step 35, assuming that the vessel fluid undergoes Newtonian flow and laminar flow, the blood density and flow viscosity may be set to conform to the physiological characteristics of the human body, and transient flow may be calculated until a result is converged. A 3D CFD solver may be based on the Incompressible Flow Navier-Stokes (N-S) equation set (mass and momentum conservation equation):

$$\nabla \cdot u = 0$$
$$\frac{\partial u}{\partial t} + u \cdot \nabla u = -\frac{\nabla p}{\rho} + v \nabla^2 u$$

where u is the fluid speed vector, p is pressure, ρ is fluid density, and v is the motion viscosity of the fluid.

In step 36, based on the 3D CFD result and using the relational expression FFR=$p_d/p_a$ (where $p_d$ is the pressure of an individual point, and $p_a$ is the average pressure at the aorta), the FFRs of all the points may be obtained. The FFR value of the distal section at the stenosis may be reported as a final calculation value, and if the FFR is less than or equal to 0.8, it may indicate that stenosis may cause functional ischemia of the vessel, and an intervention treatment may be needed. The 3D CFD result may further include other parameters of clinical interest, such as the FFR pull-back curve, blood flow rate and pressure distribution, flow distribution of each branch of the vessel, the shear stress of the vessel wall and the like.

Embodiments of the present disclosure integrate and automate the calculation process, including medical image processing, reconstruction of the calculation model, post-processing of the calculation itself and the result, resulting in rapid and accurate calculation of large batches of images.

Figure 4:
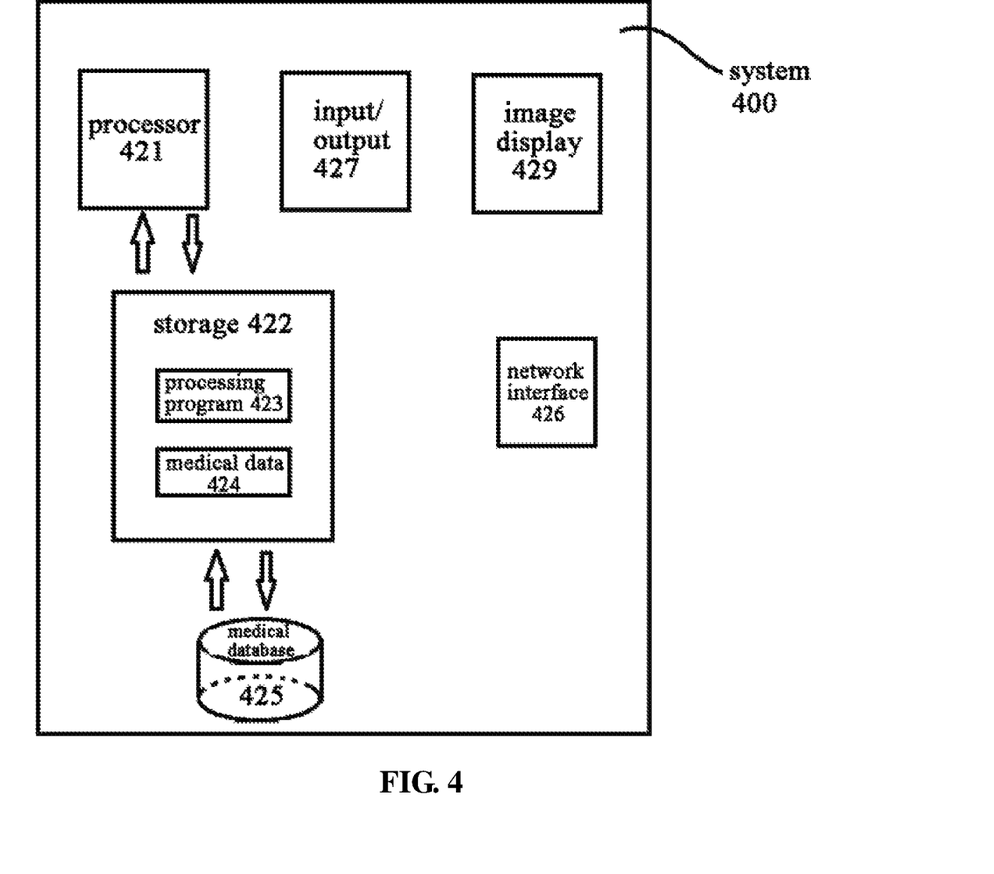
FIG. 4 is an illustration of a system for calculating vessel flow parameters based on angiography, according to an exemplary embodiment of the disclosure.

FIG. 4 is an illustration of an exemplary system for calculating vessel flow parameters based on angiography. As will be appreciated by those skilled in the art, in some embodiments, system 400 may be a special-purpose computer or a general-purpose computer. For example, system 400 may be a computer customized for a hospital for image data acquisition and image data processing, or a server placed in the cloud. In another example, system 400 may be integrated in an imaging device that collects sequences of angiographic image frames for a patient. For example, it may be integrated into a digital angiographic imaging device.

As used herein, angiography refers to a medical imaging technique that images volumes inside (i.e., lumen) of blood vessels, organs, or the like (e.g., arteries, veins, heart chambers, etc.). In one example, angiography may be performed by injecting a radio-opaque contrast agent into a vessel and imaging the vessel using one or more X-ray based techniques, such as fluoroscopy. In another example, angiography may be performed by injecting a radiopharmaceutical into a vessel and imaging the resultant vessel using a gamma camera. In yet another example, angiography may be performed by injecting radiocontrast into a vessel and imaging the resultant vessel using a high speed CT scanner. In a fourth example, angiography may be performed by injecting a contrast agent into a vessel and imaging the vessel using magnetic resonance imaging (MRI).

Accordingly, in some embodiments, the angiographic imaging device may comprise one or more light or radiation sources (such as an X-Ray source, a magnetic source, or the like) coupled with one or more imaging devices (such as a camera, magnetic flux receiving devices, or the like). In other embodiments, the angiographic imaging device may comprise only one or more imaging devices (such as a gamma camera) to detect radiation from a self-emitting (e.g., radioactive) contrast agent. Optionally, the angiographic imaging device may include one or more processors for processing data from the one or more imaging devices into digital images. Although not depicted in FIG. 4, system 400 may receive angiographic images from the angiographic imaging device.

System 400 may include a processor 421 and a memory 422. In some embodiments, as shown in FIG. 4, system 400 may additionally include at least one of a medical database 425, an input/output 427, a network interface 426 and image display 429.

Processor 421 may be a processing device that includes one of more general processing devices, such as a microprocessor, a central processing unit (CPU), a graphics processing unit (GPU), and the like. More specifically, processor 421 may be a complex instruction set computing (CISC) microprocessor, a reduced instruction set computing (RISC) microprocessor, a very long instruction word (VLIW) microprocessor, a processor running other instruction sets, or a processor that runs a combination of instruction sets. Processor 421 may also be one or more dedicated processing devices such as application specific integrated circuits (ASICs), field programmable gate arrays (FPGAs), digital signal processors (DSPs), system-on-chip (SoC) and the like.

Processor 421 may be communicatively coupled to memory 422 and configured to execute computer-executable instructions stored therein. Memory 422 may include a read only memory (ROM), a flash memory, random access memory (RAM), a static memory, etc. In some embodiments, memory 422 may store computer-executable instructions of one or more processing programs 423 and/or data generated when a computer program is executed. Processor 421 may execute the processing program 423 to implement the methods for calculating vessel flow parameters of the present disclosure, e.g., the embodiment described in conjunction with FIG. 1. Optionally, when executing the processing program 423, processor 421 may implement the embodiment described in conjunction with FIG. 3.

Processor 421 may also send/receive medical data 424 to/from memory 422. For example, processor 421 may receive the angiographic image frame sequence stored in the storage 422. In some embodiments, when executing the processing program 423, processor 421 may analyze and process the sequence of the angiographic image frames for a patient to select the template frames and the flowing frames and may send the identification information of the template frames and the flowing frames to memory 422. Accordingly, the template frames and the flowing frames in memory 422 may contain marks for the convenience of subsequent processing. Optionally, memory 422 may be configured to communicate with the medical database 425 to obtain the angiographic image frames sequence therefrom and/or to transmit the marked image frames (e.g., marked as template frame or flowing frame) to the medical database 425 to be acquired and used by users authorized to access the medical database 425.

The medical database 425 is optional and may include multiple devices positioned in a centralized or distributed manner. Processor 421 may communicate with the medical database 425 to read the angiographic image frames sequence into memory 422 and/or store the angiographic image frames sequence from memory 422 to the medical database 425.

The entries of the angiographic image frames sequences may be class-based and stored in memory 422 or the medical database 425. The items of the entry may include angiography date, a patient ID, a flowing frame or template frame marker, a projection angle and the like, such that the corresponding sequence of angiographic image frames may be used on demand. The medical data 424 stored in memory 422 may include various intermediate data generated via the method for calculating vessel flow parameters.

The sequence of the angiographic image frames, various intermediate data generated via the method for calculating vessel flow parameters based on angiography, and the vessel flow parameters obtained through calculation may be selectively displayed on image display 429, such that a doctor may view the data, check conveniently whether the analysis and processing performed by the computer is appropriate, and intervene and adjust the calculation when needed. For example, if the doctor sees any branch in the vessel segment between the projected positions of the front ends of the contrast in the start frame and the end frame in the 3D model, the doctor may change the selection of the start frame and the end frame, such that the vessel segment falls within a single branch of vessel, simplifying the calculation of the blood-passed-volume. In another example, the doctor may view whether the vessel segment between the projected positions of the front ends of the contrast in the start frame and the end frame in the 3D model is a vessel segment of interest and may adjust accordingly.

Although post-processing on the CFD calculation result may display FFR on image display 429 for the doctor, the doctor may also view thereon the distribution condition of various vessel flow parameters at individual positions of the whole vessel segment to facilitate a comprehensive diagnosis based on the combination of various vessel flow parameters. The case analysis report generated in step 37 may also be displayed on image display 429 for the doctor to view and print. In such examples, image display 429 may be an LCD, CRT or LED display.

The input/output 427 may be configured to allow system 400 to receive and/or send data. The input/output 427 may include one or more digital and/or analog communication devices that allow system 400 to communicate with a user or other machine. For example, the input/output 427 may include a keyboard and/or a mouse that allow the user to provide input, may include a printer, or the like.

The network interface 426 may include a network adapter, a cable connector, a serial connector, a USB connector, a parallel connector, a high speed data transmission adapter (such as optical fiber, USB 3.0, thunderbolt adapter, or the like), a wireless network adapter (such as a WiFi adapter or other telecommunication (3G, 4G/LTE, etc.) adapters) or the like. System 400 may be connected to the network through the network interface 426.

Various operations or functions are described herein, which may be implemented as software code or instructions or defined as software code or instructions. Such content may be source code or differential code (e.g., "delta" or "patch" code) that may be executed directly (e.g., "object" or "executable" form). The software implementation of embodiments described herein may be implemented via a computer-readable medium storing code or instructions therein or via a method in which a communication interface is operated to send instructions via the communication interface. The instructions may cause the machine to perform the described functions or operations and may include any mechanism for storing information in the form accessible by a machine (e.g., computing device, electronic system, etc.), such as recordable/non-recordable media (e.g., read-only memory (ROM), random access memory (RAM), disk storage media, optical storage media, flash memory devices, etc.). The communication interface may include any mechanism that interfaces with a hardwired medium, wireless medium, optical medium and the like, to communicate with another device, such as a memory bus interface, a processor bus interface, an Internet connection, a disk controller and the like. By providing configuration parameters and/or sending a signal, the communication interface may be configured to prepare the communication interface to provide a data signal describing software content. The communication interface may be accessed via one or more commands or signals sent to the communication interface.

The present disclosure also relates to a system for performing the operations herein. The system may comprise a special purpose computer, or the system may include a general purpose computer that is selectively activated or reconfigured by a computer program stored in the computer. Such a computer program may be stored in a computer readable storage medium such as, but not limited to, any type of disk including a floppy disk, an optical disk, a CDROM, a magnet-optical disk, a read only memory (ROM), a random access memory (RAM), an EPROM, an EEPROM, a magnetic card or an optical card, or any other type of medium suitable for storing electronic instructions, where the medium is coupled to a computer system bus.

The above examples are only exemplary and are not intended to limit the scope of the invention, which is defined by the claims. Features described in the detailed description may be combined with each other. Those skilled in the art may make various modifications and equivalent replacements within the essence and protection scope thereof, and such modifications and replacements may be regarded as falling in the protection scope.

The invention claimed is:

1. A device for modeling a vessel based on angiographic images acquired by an angiography imaging device, the device comprising:
   a processor; and
   a memory storing computer-executable instructions that, when executed by the processor, cause the processor to perform the following operations:

selecting a plurality of template frames of two view angles satisfying reconstruction conditions from the angiographic images to generate a 3D model for a vessel;

determining a start frame and an end frame in the plurality of angiographic images showing a contrast filling process;

determining corresponding locations of front ends of the contrast in the start frame and the end frame in the 3D model of the vessel;

calculating a vessel volume between the determined locations of the front ends in the 3D model; and determining an average blood flow rate based on the calculated volume, and a time interval between the start frame and the end frame.

2. The device of claim 1, wherein the operations further comprise: using the obtained average blood flow rate as boundary conditions for computational fluid dynamics simulation of the vessel.

3. The device of claim 1, wherein the plurality of template frames are filled with the contrast.

4. The device of claim 1, wherein the reconstruction conditions include that an angle between the two view angles is greater than or equal to a predetermined angle and further include the following condition: a vessel segment of interest is fully filled with contrast agent and vessel boundaries are visible.

5. The device of claim 1, wherein determining the start frame and the end frame is based on at least one of:
a contrast sharpness in the angiographic images;
a maximum time interval of the contrast flowing through a single branch of the vessel; and
a temporal change of pixel values near markers in the angiographic images.

6. The device of claim 1, wherein the start frame and the end frame correspond to the same view angle.

7. The device of claim 6, wherein the same view angle is one of the two view angles used to select the template frames.

8. The device of claim 1, wherein determining the corresponding locations of the front ends of the contrast in the start frame and the end frame is based on patch matching of the frames.

9. The device of claim 8, wherein determining the corresponding locations includes:
extracting multiple patches along a central line of the vessel in the template frames;
finding corresponding locations with a maximum correlation coefficient within a corresponding neighborhood in the start frame and the end frame based on the respective patches in the template frames to determine corresponding patches in the start frame and the end frame; and
determining a patch not presenting the vessel in the corresponding patches in the start frame and the end frame and determining the corresponding locations of the front ends of the contrast in the start frame and the end frame based on the determined patch.

10. The device of claim 6, wherein determining the corresponding locations of the front ends of the contrast in the start frame and the end frame is based on vessel matching between the start frame and the template frames and between the end frame and the template frames, the vessel matching including non-rigid matching or optical flow calculation.

11. A computer-implemented method for calculating a vessel flow parameter based on angiography, the method comprising:
selecting a plurality of template frames from a plurality of angiographic images of two view angles satisfying reconstruction conditions to generate a 3D model for a vessel;
determining a start frame and an end frame in the plurality of angiographic images showing a contrast filling process;
determining corresponding locations of front ends of the contrast in the start frame and the end frame in the 3D model of the vessel;
calculating a vessel volume between the determined locations of the front ends in the 3D model;
determining an average blood flow rate based on the calculated volume, and a time interval between the start frame and the end frame;
establishing a 3D computational fluid dynamics model for a segment of the vessel and setting boundary conditions thereof based the obtained average blood flow rate; and
solving the established 3D computational fluid dynamics model to obtain the vessel flow parameter at an individual position of the vessel segment.

12. The method of claim 11, further comprising using the obtained average blood flow rate as boundary conditions for the 3D computational fluid dynamics model.

13. The method of claim 11, wherein selecting the plurality of template frames comprises selecting image frames filled with the contrast.

14. The method of claim 11, wherein the reconstruction conditions include that an angle between the two view angles is greater than or equal to a predetermined angle and further include the following condition: a vessel segment of interest is fully filled with contrast agent and vessel boundaries are visible.

15. The method of claim 11, wherein determining the start frame and the end frame is based on at least one of:
a contrast sharpness in the angiographic images;
a maximum time interval of the contrast flowing through a single branch of the vessel; and
a temporal change of pixel values near markers in the angiographic images.

16. The method of claim 11, wherein the start frame and the end frame correspond to the same view angle.

17. The method of claim 16, wherein the same view angle is one of the two view angles used to select the template frames.

18. The method of claim 16, wherein determining the corresponding locations of the front ends of the contrast in the start frame and the end frame is based on patch matching of the frames.

19. The method of claim 18, wherein determining the corresponding locations includes:
extracting multiple patches along a central line of the vessel in the template frames;
finding corresponding locations with a maximum correlation coefficient within a corresponding neighborhood in the start frame and the end frame based on the respective patches in the template frames to determine corresponding patches in the start frame and the end frame; and
determining a patch not presenting the vessel in the corresponding patches in the start frame and the end frame and determining the corresponding locations of the front ends of the contrast in the start frame and the end frame in the template frames based on the determined patch.

20. The method of claim 16, wherein determining the corresponding locations of the front ends of the contrast in the start frame and the end frame is based on vessel matching between the start frame and the template frames and between the end frame and the template frames, the vessel matching using non-rigid matching or optical flow calculation.

21. The method of claim 11, further comprising writing the vessel flow parameter at the individual position of the segment into a case analysis report for reference by doctors.

22. The method of claim 11, wherein the angiographic images are collected under a resting condition, and setting the boundary conditions includes: multiplying the obtained average blood flow rate by 3-3.5 times to convert the average blood flow rate into an average blood flow rate under a hyperemia condition, and setting the boundary conditions based on the average blood flood rate under a hyperemia condition.

23. The method of claim 11, wherein the average blood flow rate between the start frame and the end frame characterizes the average blood flow in the segment.

24. The method of claim 23, determining the corresponding locations of the front ends of the contrast in the start frame and the end frame is based on the contrast filling process in the segment, such that the average blood flow rate between the start frame and the end frame characterizes the average blood flow rate in the segment.

25. The method of claim 24, wherein determining the start frame and the end frame includes at least one of:

determining the start frame and the end frame such that the contrast filling process between the start frame and the end frame passes through the entire segment without any branch; and setting an inlet marker near a start point and an outlet marker near an end point of the segment in the angiographic images, and automatically selecting the start frame and the end frame by analyzing variations of pixel values near the inlet marker and the outlet marker over time.

26. A non-transitory computer-readable storage medium storing computer executable instructions, wherein the computer-executable instructions, when executed by a processor, cause the processor to perform the following operations:

selecting a plurality of template frames from a plurality of angiographic images of two view angles satisfying reconstruction conditions to generate a 3D model for a vessel;

determining a start frame and an end frame in the plurality of angiographic images showing a contrast filling process;

determining corresponding locations of front ends of the contrast in the start frame and the end frame in the 3D model of the vessel;

calculating a vessel volume between the determined locations of the front ends in the 3D model; and determining an average blood flow rate based on the calculated volume, and a time interval between the start frame and the end frame.

* * * * *